(12) United States Patent
Akita et al.

(10) Patent No.: US 10,016,277 B2
(45) Date of Patent: Jul. 10, 2018

(54) HEART CORRECTION NET

(71) Applicants: KANAZAWA MEDICAL UNIVERSITY, Uchinada-machi, Kahoku-gun, Ishikawa (JP); Kanazawa Institute of Technology, Nonoichi-shi, Ishikawa (JP)

(72) Inventors: Toshiaki Akita, Uchinada-machi (JP); Masashi Yamabe, Nonoichi (JP); Masahiro Seto, Nonoichi (JP)

(73) Assignees: Kanazawa Medical University, Ishikawa (JP); Kanazawa Institute of Technology, Ishikawa (JP)

( * ) Notice: Subject to any disclaimer, the term of this patent is extended or adjusted under 35 U.S.C. 154(b) by 78 days.

(21) Appl. No.: 14/383,923

(22) PCT Filed: Mar. 8, 2013

(86) PCT No.: PCT/JP2013/056512
§ 371 (c)(1),
(2) Date: Sep. 9, 2014

(87) PCT Pub. No.: WO2013/133425
PCT Pub. Date: Sep. 12, 2013

(65) Prior Publication Data
US 2015/0018607 A1 Jan. 15, 2015

(30) Foreign Application Priority Data
Mar. 9, 2012 (JP) .................................. 2012-053365

(51) Int. Cl.
*A61F 2/24* (2006.01)
*D04B 37/02* (2006.01)
(Continued)

(52) U.S. Cl.
CPC .............. *A61F 2/2481* (2013.01); *D04B 1/18* (2013.01); *D04B 37/02* (2013.01);
(Continued)

(58) Field of Classification Search
CPC ........... A61B 2017/00526; A61B 17/02; A61F 2210/0004; A61F 2240/002;
(Continued)

(56) References Cited

U.S. PATENT DOCUMENTS 6,264,602 B1    7/2001   Mortier et al.
6,432,039 B1 *   8/2002   Wardle .................. A61F 2/2481
                                                     600/16
(Continued)

FOREIGN PATENT DOCUMENTS

JP     2003/526448 A    9/2003
JP     2003/532489       11/2003
(Continued)

OTHER PUBLICATIONS

English Machine Translation of JP2008161346.*
(Continued)

*Primary Examiner* — Samuel Gilbert
(74) *Attorney, Agent, or Firm* — Jenkins, Wilson, Taylor & Hunt, P.A.

(57) ABSTRACT

A heart correction net according to the present invention is attached to an exterior of a heart. The heart correction net includes a first area that is a partial area included in a right ventricle side area of an entire area surrounding exteriors of ventricles; and a second area that is an area surrounding the first area in the right ventricle side area and a left ventricle side area. The first area in the heart correction net is configured to provide a lower contact pressure against a heart during a cardiac diastole than the second area.

4 Claims, 3 Drawing Sheets

(51) Int. Cl.
*D04B 1/18* (2006.01)
*A61B 17/00* (2006.01)
*A61B 34/10* (2016.01)

(52) U.S. Cl.
CPC ............... *A61B 2017/00526* (2013.01); *A61B 2034/108* (2016.02); *A61F 2210/0004* (2013.01); *A61F 2240/002* (2013.01); *A61F 2240/004* (2013.01); *A61F 2250/0031* (2013.01); *A61F 2250/0041* (2013.01); *D10B 2509/08* (2013.01)

(58) Field of Classification Search
CPC ........ A61F 2240/004; A61F 2250/0031; A61F 2250/0041; A61F 2/2481; A61F 2/2478; D04B 1/18; D04B 37/02; D10B 2509/08; A61N 1/3627
USPC ........................................................ 600/37
See application file for complete search history.

(56) References Cited

U.S. PATENT DOCUMENTS

| | | | |
|---|---|---|---|
| 6,612,978 | B2 | 9/2003 | Lau et al. |
| 7,174,896 | B1 | 2/2007 | Lau |
| 7,468,029 | B1 | 12/2008 | Robertson, Jr. |
| 7,938,768 | B2 | 5/2011 | Shapland et al. |
| 2002/0019580 | A1 | 2/2002 | Lau et al. |
| 2002/0045800 | A1 | 4/2002 | Lau et al. |
| 2002/0151766 | A1 | 10/2002 | Shapland et al. |
| 2004/0143154 | A1 | 7/2004 | Lau et al. |
| 2004/0176658 | A1* | 9/2004 | McMurray ............ A61F 2/2481 600/37 |
| 2006/0187550 | A1 | 8/2006 | Melvin |
| 2007/0208216 | A1* | 9/2007 | Pignato ................. A61F 2/2481 600/37 |
| 2008/0021260 | A1 | 1/2008 | Criscione et al. |
| 2008/0033235 | A1 | 2/2008 | Shapland et al. |
| 2010/0274075 | A1* | 10/2010 | Girard ................... A61F 2/2481 600/37 |
| 2011/0190795 | A1* | 8/2011 | Hotter ................... A61F 2/0063 606/151 |

FOREIGN PATENT DOCUMENTS

| | | |
|---|---|---|
| JP | 2005/537871 A | 12/2005 |
| JP | 2008 161346 A | 7/2008 |
| JP | 2010/535081 A | 11/2010 |
| JP | 4528549 | 11/2010 |
| JP | 4582549 | 11/2010 |
| WO | WO-2009/018358 A2 | 2/2009 |

OTHER PUBLICATIONS

Extended European Search Report for Application No. EP 13 75 8466.0 dated Nov. 17, 2015.
Chinese Office Action for Application No. 201380013202.3 dated Jan. 12, 2016.
Japanese Office Action for Application No. 2012-053365 dated Jan. 26, 2016.
International Search report for Application No. PCT/JP 2013/056512 dated May 16, 2013.
International Preliminary Report on Patentability for Application No. PCT/JP 2013/056512 dated Sep. 9, 2014.
Written Opinion of the International Search Authority for Application No. PCT/JP 2013/056512 dated Sep. 9, 2014.
Chinese Office Action for Application No. 201380013202.3 dated Jul. 6, 2016.
Chinese Office Action for Application No. 201380013202.3 dated Feb. 3, 2017.
Chinese Office Action for Application No. 201380013202.3 dated Sep. 20, 2017.

* cited by examiner

HEART CORRECTION NET

CROSS-REFERENCE TO RELATED APPLICATIONS

The present application is filed under the provisions of 35 U.S.C. § 371 and claims the priority of International Patent Application No. PCT/JP2013/056512 filed on Mar. 8, 2013 and of Japanese Patent Application No. 2012-53365 filed on Mar. 9, 2012. The disclosures of the foregoing international patent application and Japanese patent application are hereby incorporated by reference herein in their respective entireties.

TECHNICAL FIELD

The present invention relates to a heart correction net that is attached to an exterior of a heart for treatment of a heart disease.

BACKGROUND ART

Conventionally, there is proposed a heart correction net to be attached to an exterior of a heart (see, for example, Patent Document 1) as one of the medical appliances for treatment of heart diseases. The heart correction net is a net configured by forming a mesh cloth into a cup-shaped configuration. The heart correction net of this type is attached to an exterior of an enlarged heart of a heart failure patient, in order to inhibit further cardiac dilation (cardiac remodeling) to thereby prevent deterioration of heart failure.

In a case of a heart correction net described in Patent Document 1, the net is designed on the basis of a relatively large heart so as to be attachable regardless of the size of a heart. Accordingly, during an operation, it is necessary to cut off an excess part and sew up the net in accordance with the size of a patient's heart.

However, in a case where a cut-off amount of the excess part is insufficient, the heart correction net can be a larger net relative to the heart. In this case, an effect to inhibit cardiac dilation is likely to be insufficient. In contrast, in a case where the cut-off amount is unnecessarily large, the heart correction net can be a smaller net relative to the heart. In this case, dilation failure of the heart is likely to be caused. Therefore, the cut-off amount must be set appropriately. However, there is no clear standard of the cut-off and sewing amount, and the amount is left to the subjective view of an individual surgeon. As a result, treatment results are different among different cases. Also, there has been a problem in that cut-off operation and sewing operation require time, leading to increased burdens on a patient.

In regard to these problems, the present inventors have proposed a technique to measure a three-dimensional configuration of a heart, which differs in size and shape for an individual patient and to knit a heart correction net having a form that exactly fits the individual patient (see Patent Document 2). According to the technique, a plurality of tomographic images are measured using a tomography apparatus, such as a CT (Computed Tomography) apparatus, an MRI (Magnetic Resonance Imaging) apparatus, a cardiac ultrasound diagnostic apparatus, and the like. Then, a contour of a heart (two-dimensional data) is extracted from each of the tomographic images. Further, three-dimensional data is constructed based on a plurality of contours from the tomographic images. Subsequently, pattern data created based on the three-dimensional data is inputted to a computerized knitting machine that is capable of three-dimensional knitting to thereby knit a heart correction net that exactly fits a patient's heart.

According to the heart correction net manufactured by this method, it is only required to cover a heart with the heart correction net when attaching the heart correction net to the heart. Accordingly, unlike the case of a versatile heart correction net having a larger size, it is not required to cut off an unnecessary part of the net in accordance with the size of a patient's heart during an operation. Consequently, it is possible to perform the operation rapidly without the need of cutting off the unnecessary part, which significantly shortens the operation time, and thus reduces burdens on the patient.

PRIOR ART DOCUMENTS

Patent Documents

Patent Document 1: Published Japanese Translation of PCT International Publication for Patent Application No. 2003-532489
Patent Document 2: Japanese Patent No. 4582549

SUMMARY OF THE INVENTION

Problems to be Solved by the Invention

The aforementioned heart correction net, however, still has room to be improved in terms of the points described below.

Specifically, the aforementioned heart correction net restricts ventricles from the exterior thereof, to thereby inhibit excessive dilation of a left ventricle. As a result, the heart correction net corrects the configuration of a heart, to thereby improve the contractility of the heart (left ventricle). However, in a case of restricting the ventricles from the exterior thereof, if a restricting force is too strong, not only dilation of the left ventricle is inhibited, but also dilation of a right ventricle having a thinner ventricular wall is to be inhibited to a higher extent. This might result in capacity reduction and pressure increase of the right ventricle during a diastole. Such phenomenon in the right ventricle might be a reason for right-sided heart malfunction and thus for deteriorated functions of the entire heart as represented by cardiac output.

On the other hand, it is possible to inhibit capacity reduction and pressure increase of the right ventricle if the restricting force of the heart correction net is weakened, for example, by attaching a further larger heart correction net. However, only taking such measures will result in weakening of even an operation of inhibiting dilation of the left ventricle, and thereby will result in weakening of an originally intended effect of the heart correction net.

In other words, it is extremely important in a heart correction net of this type to take a balance of appropriately inhibiting dilation of the left ventricle and not excessively restricting the right ventricle. It is not always easy, however, to take such balance according to conventional heart correction nets, and further improvements have been required in the medical field.

In the present invention, it is desirable to provide a heart correction net that is capable of inhibiting dilation of the left ventricle appropriately, while not restricting the right ventricle excessively.

Means for Solving the Problems

A heart correction net according to the present invention is a heart correction net to be attached to an exterior of a heart, which includes a first area that is a partial area included in a right ventricle side area of an entire area surrounding exteriors of ventricles; and a second area that is an area surrounding the first area in the right ventricle side area and a left ventricle side area. The first area is configured to provide a lower contact pressure against a heart during a cardiac diastole than the second area.

The second area in the heart correction net includes not only the left ventricle side area but also the area surrounding the first area in the right ventricle side area of the entire area surrounding the exteriors of the ventricles. Accordingly, even if a force from a heart is applied to a portion of the second area located on the exterior of the left ventricle, a portion located in the area surrounding the first area inhibits the portion of the second area located on the exterior of the left ventricle from being shifted in a dilation direction of the heart, and thus it is possible to appropriately inhibit dilation of the left ventricle.

On the other hand, since it is possible to appropriately inhibit dilation of the left ventricle only by a configuration of the second area, any configuration for the first area may be employed without considering restriction on a left ventricle side. In the present invention, a configuration is employed in which a contact pressure against a heart during a cardiac diastole is lower than that in the second area. With such configuration, inhibition of dilation of the right ventricle is weakened in accordance with the reduction in contact pressure against a heart in the first area, and thus it is possible to avoid capacity reduction and pressure increase of the right ventricle.

It should be noted that even if the heart correction net is simply divided into a left ventricle side and a right ventricle side, and the left ventricle side has a poorly stretchable configuration and the right ventricle side has a highly stretchable configuration, the aforementioned effect cannot be expected. This is because if, when a portion of the right ventricle side is stretched following the dilation of a heart, a portion of the left ventricle side is shifted in the dilation direction of the heart by a stretched amount of the portion of the right ventricle side, the contact pressure will be reduced also in the portion of the left ventricle side. In contrast, in the case of the present invention, since the second area includes not only the left ventricle side area but also the area surrounding the first area in the right ventricle side area, it is possible to appropriately secure the contact pressure on the left ventricle side, unlike the case in which simply the entire right ventricle side is stretchable.

In the heart correction net according to the present invention, various specific configurations for the first area may be devised as long as the first area is configured to provide a lower contact pressure against a heart in a cardiac diastole than the second area. In a typical example of the configuration for the first area, it is preferable, for example, that a through hole penetrating between an inside and an outside of the heart correction net is provided in the first area. In other words, the first area is preferably an area in which the through hole penetrating between the inside and the outside of the heart correction net is provided.

According to the heart correction net configured as above, since no restriction by the net is imposed in the first area, the pressure applied on the exterior of the right ventricle is reduced accordingly although some extent of restriction by the net may be imposed around the first area. Therefore, inhibition of dilation of the right ventricle is weakened in accordance with the reduction in pressure, and thus it is possible to avoid capacity reduction and pressure increase of the right ventricle.

Other than the aforementioned through hole, it may be possible to employ, for example, a configuration in which the first area is knitted with an absorbable yarn to be decomposed and eliminated in a body, and the second area is knitted with a non-absorbable yarn not to be decomposed but to remain in a body, wherein the first area provides a lower contact pressure against a heart during a cardiac diastole than the second area as a result of decomposition of the absorbable yarn.

According to the heart correction net configured as above, after the attachment to a heart, the net is decomposed and eliminated so that no restriction by the net is imposed in the first area that is knitted with an absorbable yarn. On the other hand, the net is not decomposed and an intended restricting force remains in the second area that is knitted with a non-absorbable yarn. Thus, it is possible not to impose excessive restriction on the right ventricle, while appropriately inhibiting dilation of the left ventricle.

Alternatively, the first area may be knitted with a hybrid-type yarn that is knitted with an absorbable yarn and a non-absorbable yarn. In this case, the non-absorbable yarn remains after the absorbable yarn is decomposed in a body, and thus it is possible to maintain a moderate restriction by the non-absorbable yarn for a long time period.

Further, the present invention may be employed either in a versatile heart correction net prepared without taking individual differences of patients into consideration or in a tailor-made type heart correction net prepared taking individual differences of patients into consideration; however, the latter case is more preferable considering burdens and effects on patients.

Specifically, it is preferable that the heart correction net of the present invention is formed by taking a plurality of tomographic images of a heart as an imaging target using a tomography apparatus; extracting tomographic images corresponding to an end diastole of a heart from the respective tomographic images and extracting a contour of the heart included in the extracted tomographic images; creating three-dimensional data representing a three-dimensional configuration of the heart based on the extracted contour; and providing knitting data, which is created based on the three-dimensional data, to a knitting machine that is capable of knitting a knitting yarn into a three-dimensional configuration based on the knitting data, to thereby knit a knitted fabric having a configuration that fits the heart.

According to the heart correction net configured as above, the knitted fabric has a configuration that fits a three-dimensional configuration of an application target region, and thus a heart correction net can be achieved that is fittable to an individual patient even when there are individual differences of patients in terms of size and configuration of application target region. To attach the heart correction net, therefore, it is only necessary to cover a heart with the heart correction net; it is not required to cut off an unnecessary part depending on the size of a patient's heart during an operation unlike a versatile heart correction net manufactured in a larger size. Accordingly, it is possible to rapidly perform an operation without such need and significantly shorten the operation time, and thus it is possible to reduce burdens on the patient.

Hereinafter, embodiments of the present invention will be described by way of example with reference to the drawings.

Figure 1:
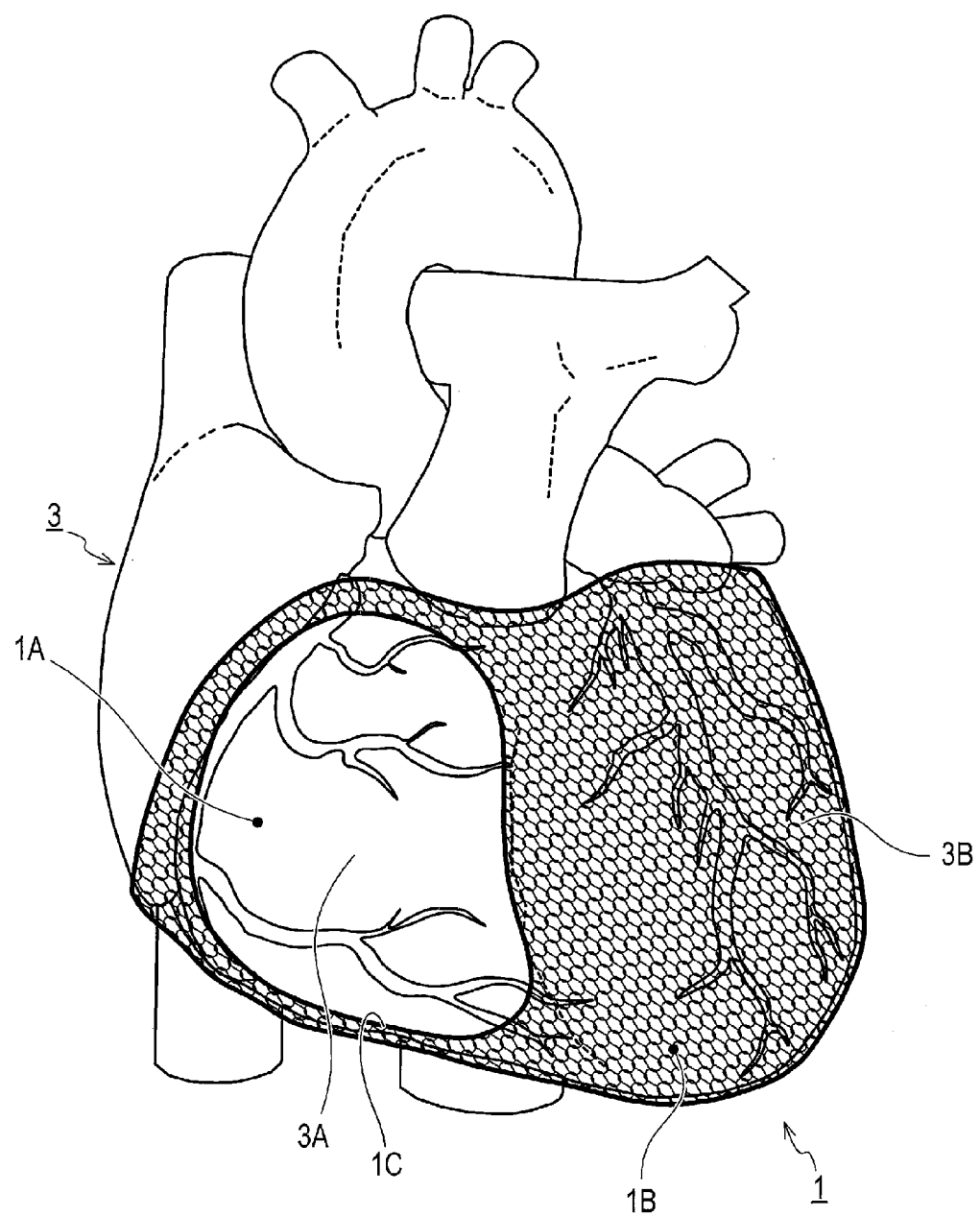
FIG. 1 is a perspective view showing a heart correction net that is illustrated as a first embodiment in a state attached to a heart.

EXPLANATION OF REFERENCE NUMERALS 1, 31 . . . heart correction net; 1A, 31A . . . first area; 1B, 31B . . . second area; 1C . . . through hole; 3 . . . heart; 3A . . . right ventricle; 3B . . . left ventricle; 11 . . . nuclear magnetic resonance diagnostic apparatus; 11' . . . multidetector-row CT diagnostic apparatus; 12 . . . image processing workstation; 14 . . . cardiac ultrasound examination apparatus; 20 . . . CAD workstation; 21 . . . CAD workstation for knitting machine; 22 . . . computer-controlled flat knitting machine.

MODE FOR CARRYING OUT THE INVENTION

First Embodiment

As shown in FIG. 1, a heart correction net 1 illustrated as a first embodiment is a medical device attached to an exterior of a heart 3 to inhibit excessive dilation of the heart 3.

The heart correction net 1 includes a first area 1A and a second area 1B. In an entire area surrounding exteriors of ventricles, a partial area included in a right ventricle 3A side area is a first area 1A; an area surrounding the first area 1A in the right ventricle 3A side area and a left ventricle 3B side area are a second area 1B. The heart correction net 1 is configured such that a contact pressure against a heart during a cardiac diastole is lower in the first area 1A than in the second area 1B.

More specifically, in the first embodiment, the first area 1A includes a through hole 1C penetrating between an inside and an outside of the heart correction net 1. Accordingly, in a state where the heart correction net 1 is attached to the heart 3, an outer surface (a region corresponding to an exterior of the right ventricle 3A) of the heart 3 is exposed through the through hole 1C in the first area 1A. By providing such through hole 1C, the contact pressure between the heart correction net 1 and the heart 3 during a cardiac diastole can be made lower in the first area 1A than in the second area 1B.

It is unnecessary to adjust the shape and size of the through hole 1C excessively strictly as long as the contact pressure to be applied on a right ventricle 3A side can be reduced. However, since the through hole 1C having an excessively small size cannot sufficiently reduce the contact pressure to be applied on the right ventricle 3A side, it is desirable that the through hole 1C has an appropriate size. On the contrary, if the through hole 1C has an excessively large size, an attachment position of the heart correction net 1 is susceptible to shift toward a left ventricle 3B side, and thereby the contact pressure applied on the left ventricle 3B side is likely to be reduced.

Accordingly, it is preferable that an area, which allows the exterior of the right ventricle 3A to be exposed sufficiently within a range where the attachment position of the heart correction net 1 is not shifted excessively toward the left ventricle 3B, is defined as the first area 1A, and the through hole 1C is formed in the first area 1A. Generally, it is preferable to set the shape and size of the through hole 1C such that a portion surrounding the through hole 1C contacts exactly around the right ventricle 3A.

When the second area 1B includes not only the left ventricle 3B side area but also the area surrounding the first area 1A in the right ventricle 3A side area of the entire area surrounding the exteriors of the ventricles, as described above, it is possible to inhibit the attachment position of the heart correction net 1 from being shifted toward the left ventricle 3B side even during a diastole of the left ventricle 3B, and thus it is possible to inhibit dilation of the left ventricle 3B appropriately.

On the other hand, in the first area 1A in which the through hole 1C is provided, the contact pressure against the heart during a cardiac diastole is lower than that in the second area 1B. Accordingly, dilation is not inhibited so much on the right ventricle 3A side as on the left ventricle 3B side, and thus it is possible to inhibit capacity reduction and pressure increase of the right ventricle 3A.

It is to be noted that although FIG. 1 shows a knitted fabric having square meshes as a knitted fabric for the heart correction net 1, this is merely for convenience to simplify the figure and does not illustrate a specific configuration of actual meshes.

In the present embodiment, the heart correction net 1 is manufactured by taking images of a three-dimensional configuration of the heart 3 having an individual difference for each patient by means of a tomography apparatus (e.g., an MRI apparatus, or the like) and by knitting a net having a configuration that exactly fits the measured configuration by means of a computer-controlled knitting machine.

Figure 2:
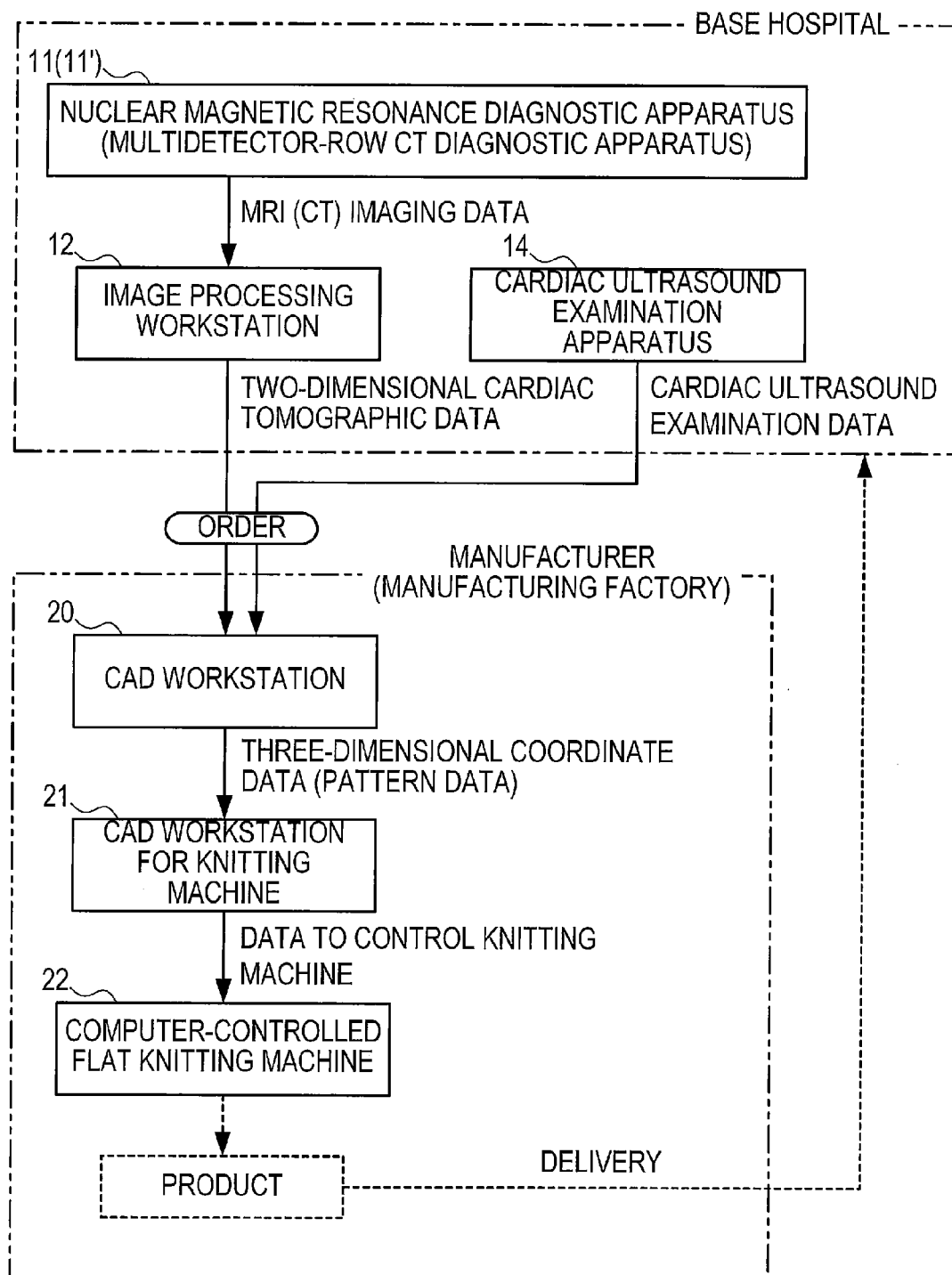
FIG. 2 is an explanatory view showing pieces of manufacturing equipment for the heart correction net.

More specifically, as shown in FIG. 2, pieces of manufacturing equipment for the heart correction net 1 include a nuclear magnetic resonance diagnostic apparatus 11 (hereinafter also referred to as an MRI 11) (or a multidetector-row CT diagnostic apparatus 11' (hereinafter also referred to as an MDCT 11')), an image processing workstation 12 (hereinafter also referred to as a workstation 12), a cardiac ultrasound examination apparatus 14 (hereinafter also referred to as an examination apparatus 14), a CAD workstation 20 (hereinafter also referred to as a workstation 20), a CAD workstation for knitting machine 21 (hereinafter also referred to as a workstation 21), a computer-controlled flat knitting machine 22 (hereinafter also referred to as a knitting machine 22), and the like.

Among these pieces of equipment, the MRI 11 (or the MDCT 11'), the workstation 12, and the examination apparatus 14 are those installed in a base hospital that is an orderer of the heart correction net 1. The workstation 20, the workstation 21, and the knitting machine 22 are those installed in a manufacturer (manufacturing factory) that manufactures the heart correction net 1.

As is well known, the MRI 11 is an apparatus to take tomographic images of a human body using nuclear magnetic resonance. Also, as is well known, the MDCT 11' is an apparatus to take tomographic images of a human body using X-rays. Either of the MRI 11 and the MDCT 11' may be used.

The workstation 12 is an apparatus to perform data processing of tomographic image data (MRI imaging data or CT imaging data) taken by the MRI 11 (or the MDCT 11'). In the present embodiment, cardiac tomographic image data (cardiac MRI image data or cardiac CT images) are extracted in the workstation 12. In the present embodiment, thirty frames/second of images are taken during imaging operation, an end diastole is specified based on electrocardiogram data, and only image data for the end diastole are extracted.

The examination apparatus 14 is an apparatus to examine the configuration of a heart based on ultrasonic wave reflection. The examination apparatus 14 is used to recognize the configuration of the heart more accurately by its combined use with the MRI 11 (or the MDCT 11'). Also, by accurately diagnosing individual clinical conditions of patients suffering from mitral valve insufficiency using the examination apparatus 14, it is possible to determine suitability of application of a treatment by the heart correction net 1, to set a plication amount of a mitral valve by the heart correction net 1, and to set a plication amount of the minor axis of the heart at the papillary muscle level.

The workstation 20 is an apparatus to perform data processing based on data transmitted from the workstation 12 and the examination apparatus 14. The workstation 20 include, as software for data processing, three-dimensional image forming software, versatile CAD software, pattern creation software, and the like.

In the workstation 20, it is also possible to set correction values, for example, to adjust the plication amount of the heart based on cardiac ultrasound data obtained from the examination apparatus 14. Data required to set the correction values includes left ventricular end-diastolic diameter (LVDd), left ventricular end-systolic diameter (LVDs), left ventricular long-axis diameter, mitral valve annulus diameters (shorter diameter, longer diameter), papillary muscle attachment position, a deviation amount of mitral valve joining position during systole (tethering or tenting: a vertical distance between a line connecting the anterior and posterior annuli of the mitral valve and the joining region of mitral valve leaflets), reverse flow volume through the mitral valve (assessed based on a long axis view), reverse flow region (assessed based on a short axis view), and the like. By making corrections based on the aforementioned various data, correction to such data that is considered to be optimal for each case is achieved.

Since the outer contour of the heart can be more accurately calculated from MD-CT images, the outer contour is measured based on MD-CT images without performing correction based on cardiac ultrasound examination data. In other words, optimal data is constructed by utilizing respective advantages of the MRI 11 (or the MDCT 11') and the examination apparatus 14. Matters such as whether to perform correction based on cardiac ultrasound examination data and, if performed, what extent of correction should be optimal, are considered, for example, through collaborative work by a cardiac surgeon and a person in charge of image processing at a manufacture side. Also, a discussion with the orderer (a cardiac surgeon at the base hospital side) is made when necessary, and then data that is considered to be optimal for an individual case is ultimately completed.

In the workstation 20, pattern data (knitting data) for knitting a heart correction net is created by two-dimensionally developing the three-dimensional configuration of the heart (three-dimensional data) that is corrected after being extracted. The workstation 21 is an apparatus to control the knitting machine 22 based on the two-dimensional pattern data (a bitmap format file) transmitted from the workstation 20.

The knitting machine 22 is an apparatus to knit a knitting yarn into a fabric having a three-dimensional configuration in accordance with instructions from the workstation 21. In the present embodiment, a WHOLEGARMENT (Registered Trademark) computerized flat knitting machine (Product Name: SWG041, made by SHIMA SEIKI MFG., LTD.) is used as the knitting machine 22.

As the knitting yarn, a knitting yarn made of a biologically compatible material is used. There is no particular limitation to specific materials or thickness of the knitting yarn as long as the knitting yarn has performance (mechanical strength, chemical strength, stretchability, and the like) that complies with the purpose of use of the heart correction net 1. Examples may include those formed by twisting non-absorbable monofilaments of polyester, polytetrafluoroethylene, foamed polytetrafluoroethylene (foamed PTFE, ePTFE), polypropylene, poly-2 fluorinated ethylene (vinylidene fluoride-hexafluoropropylene), or the like; those formed by twisting absorbable monofilaments of polyglactin, polyglycolic acid, polyethylene glycol, polylactic acid, polylactide, polyglycolide, polycaprolactone, multi-anhydrides, polyamide, polyurethane, polyesteramide, polyorthoester, polydioxanone, polyacetal, polyketal, polycarbonate, polyorthoester, polyphosphazene, polyhydroxy butyrate, polyhydroxy valerate, polyalkylene oxalate, polyalkylene succinate, poly(methyl vinyl ether), poly(maleic anhydride), poly(amino acid), and copolymer, compound, or mixture thereof; and hybrid-type yarns by combining the above. It may be possible to use only one type, or two or more types, of knitting yarn formed of these materials.

Among the aforementioned pieces of equipment, the MRI 11 (or the MDCT 11'), the workstation 12, and the examination apparatus 14 are operated by a cardiac surgeon, a cardiologist, or a radiologist at the base hospital side. As a result, two-dimensional tomographic data of the heart (DICOM data) and cardiac ultrasound examination data are prepared at the base hospital side. The two-dimensional tomographic data and the cardiac ultrasound examination data are transmitted to the manufacturer (the manufacturing factory) through a communication line.

At the manufacturer (the manufacturing factory) side, various data transmitted from the base hospital side is received, and the aforementioned data processing in the workstation 20 is performed. When knitting data based on three-dimensional data is completed in the workstation 20, the knitting data is transmitted to the workstation 21.

The workstation 21 and the knitting machine 22 are operated by a person in charge at the manufacturer side, and the heart correction net 1 having a configuration represented by the knitting data is manufactured by knitting the knitting yarn based on the knitting data. The manufactured heart correction net 1 is immediately delivered to the base hospital as the orderer and then is used.

Second Embodiment

Figure 3:
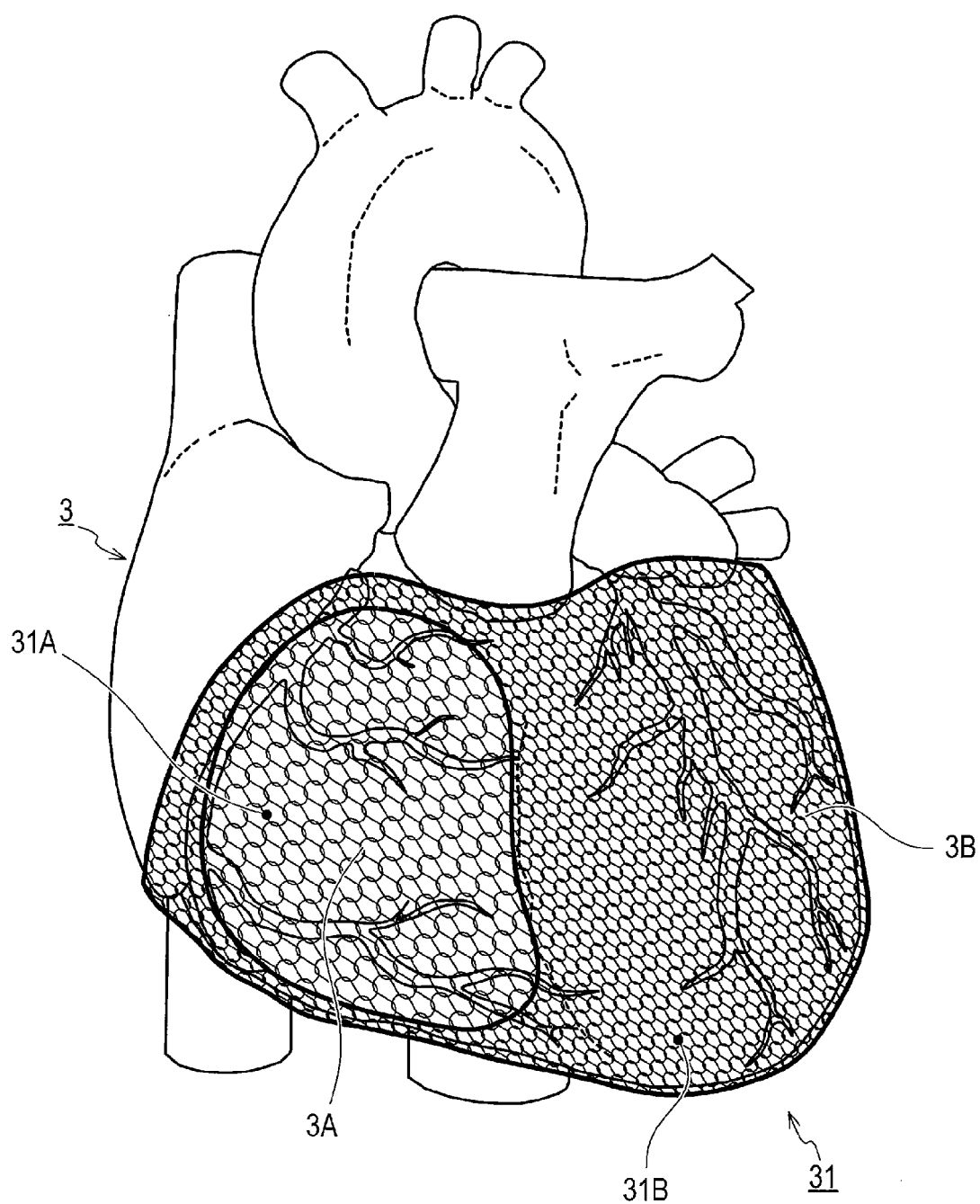
FIG. 3 is a perspective view showing a heart correction net that is illustrated as a second embodiment in a state attached to a heart.

As shown in FIG. 3, a heart correction net 31 illustrated as a second embodiment is a medical device attached to the exterior of the heart 3 in the same manner as in the first embodiment. Also in the case of the heart correction net 31, in an entire area surrounding the exteriors of ventricles, a partial area included in a right ventricle 3A side area is a first area 31A; an area surrounding the first area 31A in the right ventricle 3A side area and a left ventricle 3B side area are a second area 31B. The heart correction net 31 is also configured such that a contact pressure against a heart during a cardiac diastole is lower in the first area 31A than in the second area 31B. These features are the same as in the first embodiment.

However, the second embodiment, in which a net knitted with an absorbable yarn is provided in the first area 31A, is different from the first embodiment, in which the through hole 1C is provided. On the other hand, a net knitted with a non-absorbable yarn is provided in the second area 31B, which is equivalent to the first embodiment.

When the heart correction net 31 configured as above is attached to the heart 3, the net knitted with the absorbable yarn is present even in the first area 31A immediately after the attachment thereof. When a predetermined time period (for example, approximately two weeks, which varies depending on the thickness and material of the absorbable yarn) has elapsed after the attachment, the absorbable yarn in the first area 1A is decomposed, and a through hole is formed in the first area 1A in the same manner as in the heart correction net 1 shown in the first embodiment. Accordingly, the contact pressure against the right ventricle is reduced in the first area 1A, and the same operation and effects as in the heart correction net 1 according to the first embodiment can be achieved.

Specifically, the second area 31B includes not only the left ventricle 3B side area but also the area surrounding the first area 31A in the right ventricle 3A side area of the entire area surrounding the exteriors of the ventricles. Accordingly, it is possible to inhibit the attachment position of the heart correction net 31 from being shifted toward the left ventricle 3B side even during a diastole of the left ventricle 3B, and thus it is possible to inhibit dilation of the left ventricle 3B appropriately.

On the other hand, in the first area 31A, the contact pressure against the heart during a cardiac diastole is lower than in the second area 31B since a portion formed with the absorbable yarn is decomposed and a through hole is formed. Accordingly, dilation is not inhibited so much on the right ventricle 3A side as on the left ventricle 3B side, and thus it is possible to inhibit capacity reduction and pressure increase of the right ventricle 3A.

Also, in the case of the second embodiment, in which the heart correction net 31 is present even in the first area 31A immediately after the attachment of the net, it is easier to stabilize the configuration of the first area 31A as compared with the case of the first embodiment, in which the first area 1A is the through hole 1C prior to the attachment to the heart. Accordingly, it is easier to perform a positioning operation of the first area 31A with respect to the heart 3, and an improved effect of inhibiting positional deviation after the positioning operation can be achieved.

The material of the second area 31B formed with the non-absorbable yarn may be polyester, polytetrafluoroethylene, foamed polytetrafluoroethylene (foamed PTFE, ePTFE), polypropylene, poly-2 fluorinated ethylene (vinylidene fluoride-hexafluoropropylene), and the like, as in the first embodiment. Also, the material for the first area 31A formed with the absorbable yarn may be any of natural materials and synthetic materials, and a typical example may include polyglycolic acid.

Other Embodiments

Although some embodiments of the present invention have been described as above, the present invention is not to be limited to the above-described specific embodiments but may be practiced in other various forms.

For example, although a net knitted with an absorbable yarn is provided in the first area 31A in the above-described second embodiment, the first area 31A may be formed of a non-absorbable yarn as long as the contact pressure on the right ventricle 3A side can be reduced. In other words, whether a through hole is provided in the first area 1A, 31A is optional in the present invention, and the contact pressure on the right ventricle 3A side may be reduced by a structure other than a through hole.

A specific example of such structure may include, for example, one in which only the first area is knitted by a knitting method providing high stretchability or knitted with a highly stretchable yarn than the second area. Also, the first area may be knitted such that the net is designed to have a configuration swollen outward in a dome shape, and thereby a gap is formed between the net and the outer surface of the heart.

The invention claimed is:

1. A heart correction net to be attached to an exterior of a heart, comprising:
a net configured to surround exteriors of ventricles of a heart and comprising a first area and a second area;
wherein the first area is a partial area of the net and is configured to be included in a right ventricle side area of the exteriors of the ventricles;
wherein the first area consists of a single through hole or is configured to be decomposed in a body to thereby form the single through hole, the single through hole having a shape and a size exactly around the right ventricle such that the single through hole allows an exterior of the right ventricle side area of the ventricles to be sufficiently exposed through the net to suppress an attachment position of the heart correction net from being shifted toward a left ventricle side area of the ventricles; and
wherein the second area is configured to be included in the right ventricle side area and the left ventricle side area of the exteriors of the ventricles;
wherein the first area has an outer periphery entirely surrounded by the second area, wherein the outer periphery has a shape and a size exactly around the right ventricle; and
wherein the first area is configured to provide a lower contact pressure against the exterior of the heart during a cardiac diastole than the second area.

2. The heart correction net according to claim 1, wherein the first area comprises a through hole penetrating between an inside and an outside of the heart correction net.

3. The heart correction net according to claim 1,
wherein the first area is knitted with an absorbable yarn to be decomposed and eliminated in a body,
wherein the second area is knitted with a non-absorbable yarn not to be decomposed but to remain in a body, and
wherein the first area provides a lower contact pressure against a heart during a cardiac diastole than the second area as a result of decomposition of the absorbable yarn.

4. The heart correction net according to claim 1,
wherein the heart correction net is formed by taking a plurality of tomographic images of a heart as an imaging target using a tomography apparatus; extracting tomographic images corresponding to an end diastole of the heart from the respective tomographic images and extracting a contour of the heart included in the extracted tomographic images; creating three-dimensional data representing a three-dimensional configuration of the heart based on the extracted contour; and providing knitting data, which is created based on the three-dimensional data, to a knitting machine that is capable of knitting a knitting yarn into a three-dimensional configuration based on the knitting data, to thereby knit a knitted fabric having a configuration that fits the heart.

* * * * *